(12) United States Patent
Caffey et al.

(10) Patent No.: US 6,635,085 B1
(45) Date of Patent: Oct. 21, 2003

(54) HEART VALVE STENT WITH ALIGNMENT POSTS

(75) Inventors: James Charles Caffey, Marble Falls, TX (US); Riyad Moe, Austin, TX (US); Matthew Allen Freund, San Antonio, TX (US); James Hutton, Pflugerville, TX (US)

(73) Assignee: Carbomedics Inc., Austin, TX (US)

( * ) Notice: Subject to any disclaimer, the term of this patent is extended or adjusted under 35 U.S.C. 154(b) by 284 days.

(21) Appl. No.: 09/640,599

(22) Filed: Aug. 17, 2000

(51) Int. Cl.⁷ .................................. A61F 2/24
(52) U.S. Cl. ................. 623/2.1; 623/2.14; 623/2.17; 623/2.19; 623/900
(58) Field of Search ................. 623/1.15, 1.24, 623/900, 2.1, 2.14, 2.17, 2.19

(56) References Cited

U.S. PATENT DOCUMENTS

| | | | | |
|---|---|---|---|---|
| 3,755,823 A | * | 9/1973 | Hancock | 623/2.18 |
| 4,343,048 A | * | 8/1982 | Ross et al. | 623/2.14 |
| 4,501,030 A | * | 2/1985 | Lane | 623/2.18 |
| 4,626,255 A | * | 12/1986 | Reichart et al. | 623/2.13 |
| 5,728,152 A | * | 3/1998 | Mirsch et al. | 623/2.1 |
| 5,840,081 A | * | 11/1998 | Andersen et al. | 606/108 |
| 6,458,156 B1 | * | 10/2002 | Wan et al. | 623/2.14 |
| 6,485,510 B1 | * | 11/2002 | Camrud et al. | 623/1.16 |

* cited by examiner

Primary Examiner—Michael J. Milano
Assistant Examiner—Gwen Phanijphand
(74) Attorney, Agent, or Firm—Timothy L. Scott

(57) ABSTRACT

A stent includes a stent member having a plurality of post members formed therein. Each post member is connected to an adjacent post member by an interconnecting portion. A plurality of leg members extend from the stent member. The stent may be molded within a flexible polymer valve. The legs stabilize and locate the stent in the mold. Upon completion of the molding process, the legs can be separated from the stent.

21 Claims, 3 Drawing Sheets

HEART VALVE STENT WITH ALIGNMENT POSTS

BACKGROUND

The disclosures herein relate generally to flexible leaflet prosthetic heart valves and more particularly to wire stents used to reinforce such valves. Wire stents used in prosthetic heart valves are normally symmetrical in geometry. There are many known examples of such stents.

In U.S. Pat. No. 4,343,048, a stent for a cardiac valve comprises a base ring having metal legs projecting therefrom in a generally axial direction, each leg being flexible in such a manner that, when the stent has a valve installed therein and the valve is under pressure such as when operating in the heart, each respective leg can resiliently deform over substantially its whole axial length to take up strain in the valve without impairing its performance.

U.S. Pat. No. 4,501,030 discloses a prosthetic heart valve including a frame having a plurality of commissure supports, a plurality of resilient supports, and a plurality of valve leaflets. The valve leaflets are attached to the resilient supports, and the resilient supports lie radially outwardly of the commissure supports, respectively. When in use, the valve is subjected to forces which are used to clamp the valve leaflets between the resilient supports and the commissure supports to augment whatever other leaflet attachment techniques may be used.

U.S. Pat. No. 5,545,215 discloses a frame to be placed as an external support of a biological valved conduit containing three leaflets. This external frame, made of biocompatible metal or plastic, is sutured to the outer surface of the valved conduit made of biological or biocompatible membrane or sigmoid valve root in order to maintain its natural geometry. The frame has a general cylindrical configuration, circular as viewed from above and below. From a side view however, both upper and lower ends of the cylinder present three convex curvatures joined at equidistant points of the circumference. These upper and lower curves are joined by three vertical struts, so that three large saddle shaped paraboloid gaps result. The frame is a wire-like structure.

U.S. Pat. No. 4,626,255 discloses a heart valve prosthesis having a supporting frame with a circular cross-section, which is covered with a dacron fabric. On one end face, the dacron fabric is arranged to form a suture ring. The fixed aortic valve of a kangaroo is attached inside the frame and sutured to the dacron fabric.

Insert molding is a less costly method of attaching a stent to a valve body that many other methods, such as sewing and dip casting. This is especially true in high volume manufacturing. There are tight form control tolerances associated with insert molding processes for molding stents into polymer valve bodies. Despite these tolerances, the stent must fit within the cavity of the mold and remain stationary. Otherwise, the stent and mold can be damaged. Insert molding, then, is benefitted by a stent that 1) has simple features that can be held securely by the mold, and 2) has features which facilitate accurate locating of the stent in the mold. In fact, all valves, regardless of their manufacturing method, benefit from this second point, i.e. accurate location. Accurate location improves manufacturing repeatability and inspection accuracy. These lead to a more reliable product with smaller unit variability and lower manufacturing costs.

Accurate and repeatable location of a part requires defining datums. Accurate location is needed for manufacturing, assembly and inspection. A three dimensional, curvilinear part, such as a heart valve stent, complicates the method of defining these datums. One widely used method of inspection uses 6 stops on 3 mutually perpendicular datum planes to locate the part. This method, called 3-2-1 location is described in many engineering texts including "Fundamentals of Tool Design," 2nd Edition, Hoffman (Ed.), Society of Manufacturing Engineers, 1984 pp. 142–158, 170. Stops are used to define the first, usually horizontal, plane, and to locate the part against a vertical plane. Any additional stops, for example, a fourth stop on the horizontal plane, will over constrain the part and require deforming it to touch all stops. Plane on plane contact is another example of over constraint. Over constraining a part in manufacturing or inspection jeopardizes accuracy and repeatability.

The two configurations of stent, described above, do not lend themselves to accurate location. The stents with planar bottoms or horizontal grooves cannot be located reliably on a reference plane. A special locating block with three vertical projections is needed. None of the designs have features designed to be located against the vertical datum planes. The stents could be located in a V-block, but there is no feature to control rotation around the central axis. Parts must be located and inspected using visual alignment, which is time consuming, operator dependent, and coarse unless expensive optical equipment is used.

To make matters worse, many of the fabrication methods used in stents make it difficult to control form. Most designs contain an edge or surface that is curving in at least two directions. Metal bending (wireforms, rolled flat patterns, and drawn flat patterns) will exhibit springback and warping from residual stresses. Welding and crimping over constrain free ends. Injection molded plastics are subject to warping from shrink and relieved thermal stresses. Conventional machining gives rise to residual stresses that can warp parts.

Therefore, what is needed is a stent that provides for the tight form control tolerances of the insert molding process.

Summary

One embodiment, accordingly, provides a stent having features which permit the stent to be held easily and securely, and which facilitate accurate locating for insert molding a stent in a polymer valve. To this end, a stent includes a stent member having a plurality of post members formed therein. Each post member is connected to an adjacent post member by an interconnecting portion. A plurality of leg members extend from the stent member.

A principal advantage of this embodiment is that it provides for a stent to be located more accurately and held more securely than previously known stents.

BRIEF DESCRIPTION OF THE DRAWING FIGURES

DETAILED DESCRIPTION

The embodiments describe a stent with downward extending legs used as locating and capturing features during manufacturing, molding, assembly, and inspection. The stent can have one, two, three, or more than three legs. Three legs are preferred because in combination they define a locating plane. The legs can be staggered around the perimeter of the valve. Equally spaced legs are preferred for simplicity. These legs can be indefinitely long. They may be trimmed back or completely removed after molding is completed.

The stent can be a one piece member fabricated from a tube of material using conventional, laser, or electrical discharge machining (EDM). Alternatively, a flat pattern of the stent can be cut and the stent rolled and joined to form an endless trajectory. The stent could also be fabricated from bent wire. The legs can be attached by welding a wire leg to the stent, or by bending a tight "U" loop downward from the stent. A stent fabricated from a tube has the benefit of improved form control because there is no springback and no welds to inspect, or to cause local stiffness variation. Springback is the elastic recovery of a bent piece of metal.

Figure 1:
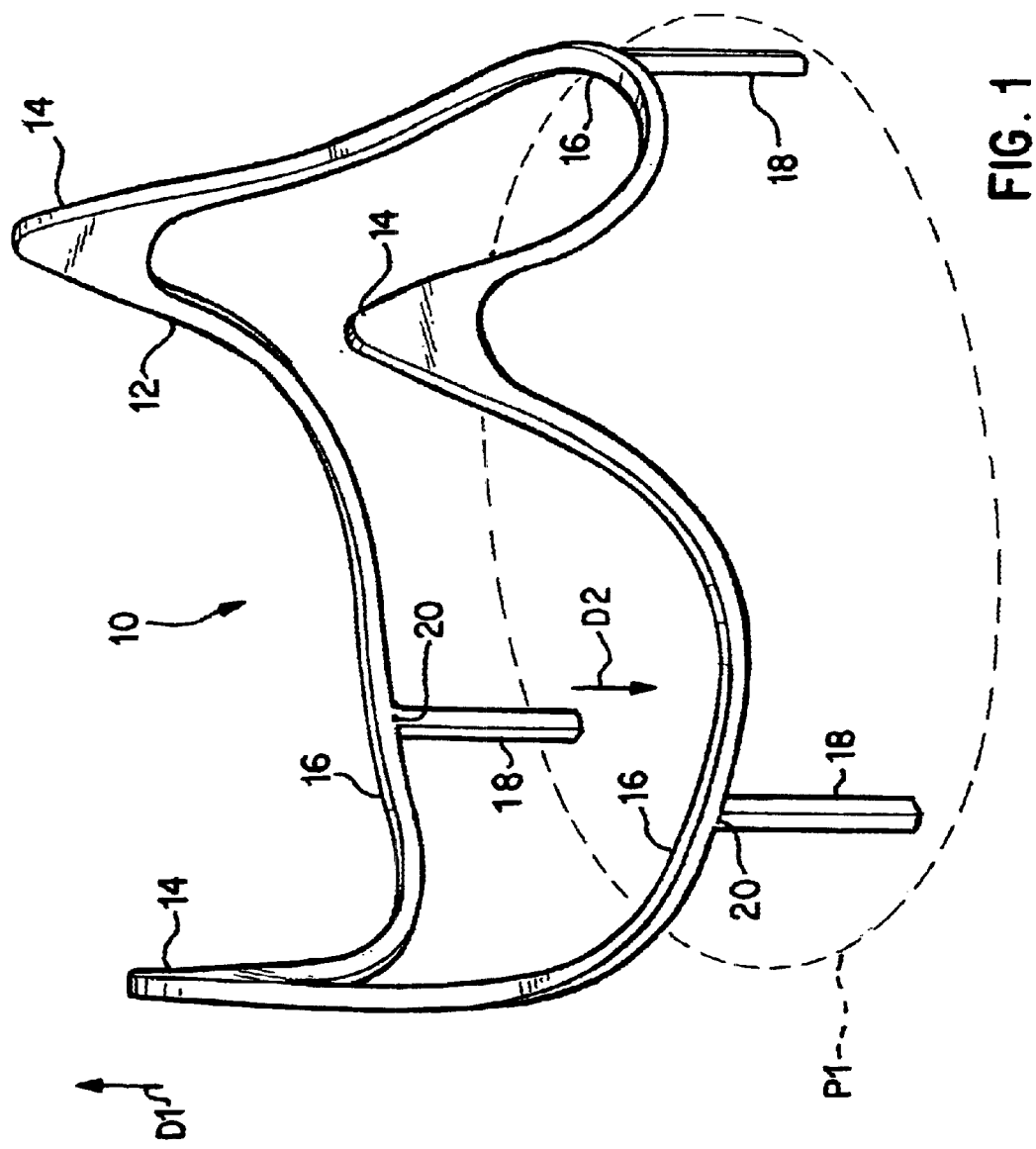
FIG. 1 is a perspective view illustrating an embodiment of a stent.

Referring to FIG. 1, a stent is generally designated 10 and includes an elongated stent member 12 which is formed to include a plurality of flexible post members 14. Each post member 14 is connected to an adjacent post member 14 by an interconnecting portions 16. Thus, in the embodiment illustrated, stent 10 includes three post members 14 interconnected by three interconnecting portion 16. Post members 14 extend in a first direction D1. A plurality of leg members 18 extend from the stent member 12, and more specifically in this embodiment, the leg members 18 extend from the interconnecting portions 16. Leg members 18 extend in a second direction D2, generally opposite the first direction D1. A break-away connection 20 may be provided on each leg member 18 adjacent the respective interconnecting portion 16. Break-away connection 20 may comprise a score on the material, as shown, or may comprise a notch or other detachment means known in the art, so as to weaken the joint between the leg member 18 and stent member 12 for ease of detaching the leg members 18 when desired. The embodiment of FIG. 1 is for use in a tri-leaflet valve, however, modification can be made for a bi-leaflet, or even a single leaflet valve. For example, a bi-leaflet valve (not shown) would include two post members 14 and two interconnecting portions 16, but would preferably include three leg members 18, because three leg members provide three points of reference to define a plane P1. This permits the seating of stent member 10 to be stabilized. Such stabilization is a valuable enhancement to stent 10 for example when seating stent 10 in a mold, or during an inspection procedure following the molding of stent 10 into a polymer heart valve, as is discussed below. By various known production methods, stent 10 may be formed (cut) from a single piece of material, or may be fabricated into a unit from several pieces of material. The preferred material for stent 10 is a titanium alloy but other material may include cobalt chrome alloys, polypropylene, or other rigid or semi-rigid polymers and composites.

Figure 2:
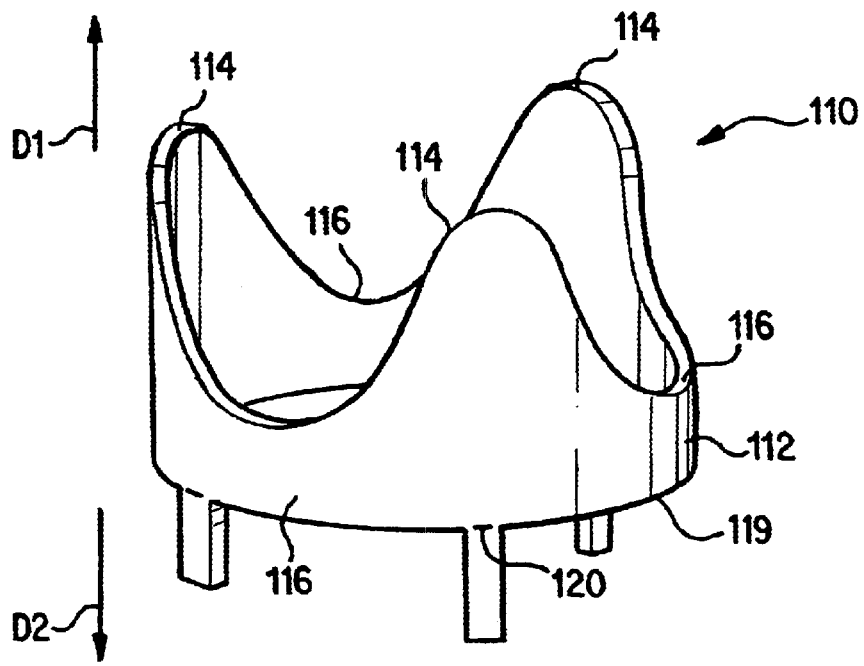
FIG. 2 is a perspective view illustrating another embodiment of a stent.

In another embodiment, FIG. 2, a stent 110 is of a modified form from that illustrated in FIG. 1, i.e. stent 110 is cut from a single piece such as a cylinder using, for example, a laser. Stent 110 includes a stent member 112 formed to include a plurality of flexible post members 114. Each post member 114 is connected to an adjacent post member by an interconnecting portion 116. In the embodiment of FIG. 2, stent member 112 includes three post members 114 interconnected by three interconnecting portions 116. Post members 114 extend in first direction D1. A plurality of leg members 118 extend from stent member 112. In this embodiment, leg members 118 do not necessarily extend from interconnecting portions 116, but may extend from a position anywhere along the surface 119 of stent member 112. Leg members 118 extend in a second direction D2, generally opposite the first direction D1. A break-away connection 120, similar to that discussed above with respect to the embodiment of FIG. 1, may be provided on each leg member 118 adjacent the connection to surface 119 of stent member 112, to weaken the joint between the leg member 118 and stent member 112, for ease of detaching the leg members 118 when desired. Although the embodiment of FIG. 2 is for use in a tri-leaflet valve, modification can be made for a bi-leaflet or even a single leaflet valve.

Figure 3:
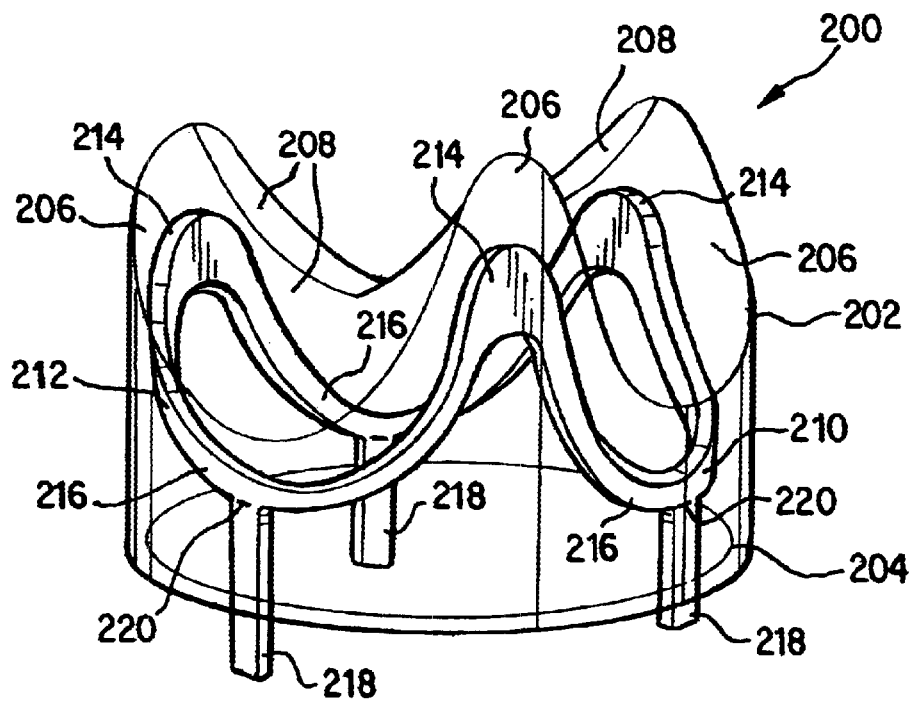
FIG. 3 is a perspective view illustrating a flexible heart valve prosthesis including a stent molded therein.

A heart valve prosthesis 200, FIG. 3, may include a flexible tri-leaflet heart valve 202 formed of a flexible polymer material, for example. Heart valve 202 may include a base 204, a plurality of valve post members 206 and a plurality of flexible leaflets 208. A stent 210 includes a stent member 212 having a plurality of flexible stent post members 214. Each stent post member 214 is connected to an adjacent stent post member 214 by an interconnecting portion 216. A plurality of leg members 218 extend from stent member 212. Leg members 218 may include a break-away connection 220 for detaching the leg members 218 from the stent member 212.

Figure 4:
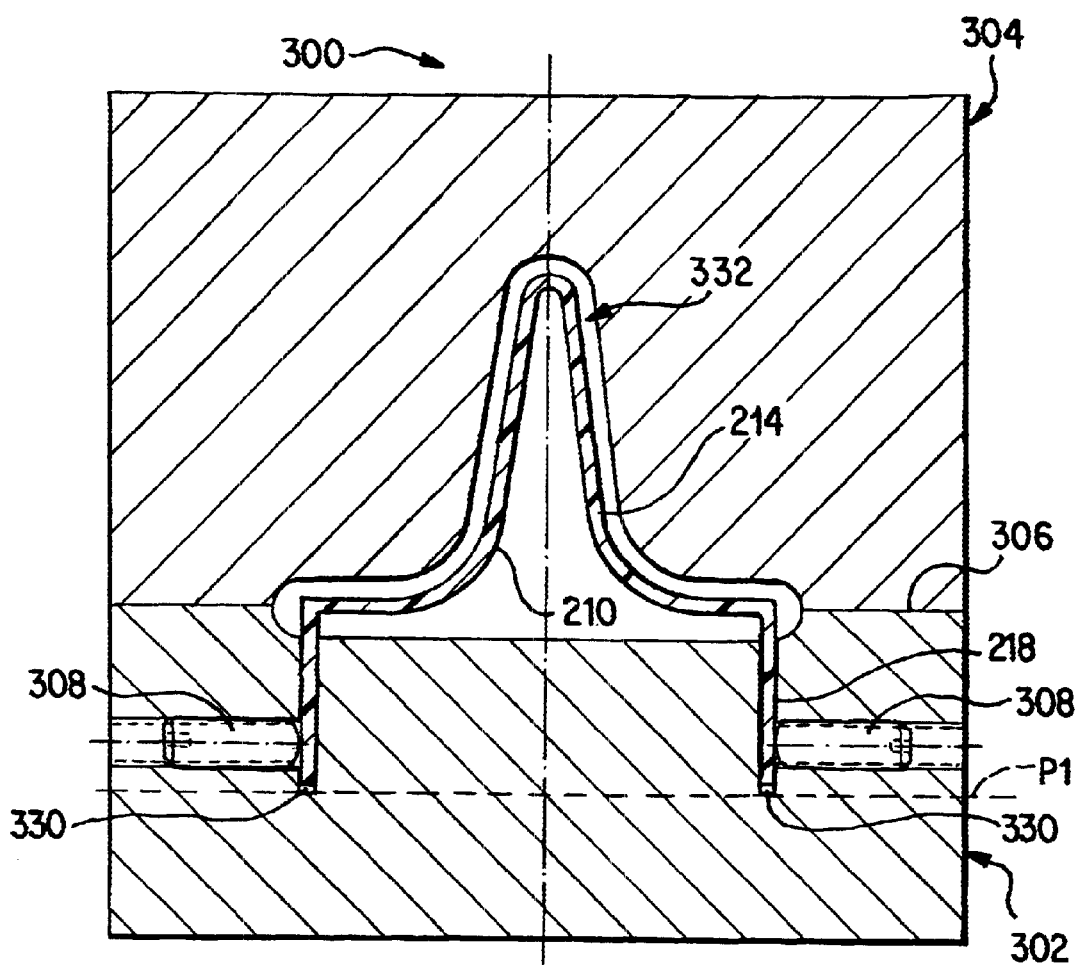
FIG. 4 is a cross-sectional side view illustrating an embodiment of a mold used for molding the stent into the flexible heart valve prosthesis.
Figure 5A:
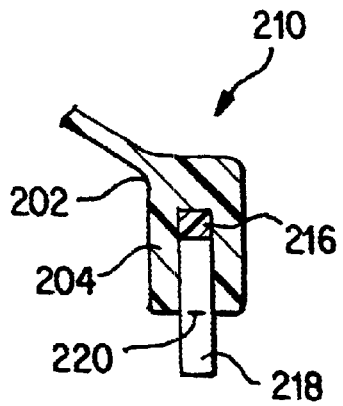
FIG. 5a is a partial cross-sectional side view illustrating an embodiment of a stent leg member protruding from a stent in a flexible heart valve.
Figure 5B:
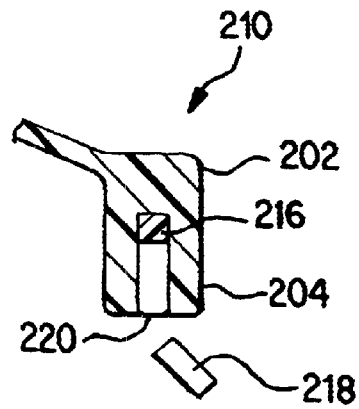
FIG. 5b is a partial cross-sectional side view illustrating the leg member of FIG. 5 being broken away from the stent in the heart valve.

Heart valve 202 may be formed in a mold 300, FIG. 4, by a well-known injection molding process. Mold 300 includes a base portion 302 and a cap portion 304 which join together at a joint 306. A plurality of set screws 308 are mounted in base portion 302. A stent 210 may be mounted in base portion 302 such that leg members 218 of stent 210 extend into base portion 302. Three leg members 218, only two of which are shown in FIG. 4, position and stabilize stent 210 in base portion 302. For example, the leg members 218 seat in respective leg cavities 330 in base portion 302. The leg cavities 330, only two of the three being shown, form a plane P1 for stabilizing stent 210 in base portion 302. Set screws 308 may be advanced to secure leg members 218 in leg cavities 330 during the molding process. Stent post members 214 extend into a mold cavity 332 in cap portion 304. Polymer material can be injected into mold cavity 332 for molding stent 210 within the heart valve 202 as illustrated in FIG. 3. Subsequent to curing, heart valve 202 may be removed from mold 330, and supported on a planar surface by leg members 218 during inspection and final processing. Leg members 218 may then be removed from the stent 210 as is illustrated in FIGS. 5a and 5b. In FIG. 5a, base portion 204 of heart valve 202 includes leg member 218 extending from interconnecting portion 216 of stent 210, and protruding from base portion 204 of heart valve 202. In FIG. 5b, leg member 218 is broken away from stent 210 at break-away connection 220.

As a result, one embodiment provides a stent including a stent member having a plurality of post members formed therein. Each post member is connected to an adjacent post member by an interconnecting portion. A plurality of leg members extend from the stent member.

Another embodiment provides a heart valve prosthesis including a heart valve formed of flexible material. A stent member is molded into the valve. A plurality of post members are formed in the stent member. Each post member is connected to an adjacent post member by an interconnecting portion. A plurality of leg members extend from the stent member.

A further embodiment provides a method of forming a stented valve. A stent is formed to include a plurality of legs extending therefrom. The legs are located on a planar surface for stabilizing the stent in a mold. The stent is injection molded within a flexible heart valve.

As it can be seen, the principal advantages of these embodiments are that it provides for a stent to be located more accurately and held more securely than previously known stents. Enhanced locatability and fixturing are coupled with manufacturing methods that reduce part variability to create a stent that provides for the tight form control tolerances of the insert molding process. The stent can be secured in a mold by seating the legs into holes and advancing set screws against the legs to secure the stent in the mold. Alternatively, plastic plugs may be placed in the holes to create an interference fit with the legs. Thus the three legs define a plane for stabilizing the stent in the mold and repeatedly positioning the stent for producing repeatable quality injection molded, stented polymer valves.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A heart valve stent comprising:
   a stent member comprising a plurality of post members, each post member being connected to an adjacent post member by an interconnecting portion; and
   a plurality of leg members extending from the stent member, wherein each leg member comprises a break-away connection to the stent member.

2. The stent of claim 1 wherein the stent comprises at least two post members.

3. The stent of claim 1 wherein the stent comprises at least two interconnecting portions.

4. The stent of claim 1 wherein the stent comprises at least three leg members.

5. The stent of claim 1 wherein the post members, the interconnecting portions and the leg members are formed from a single piece of material.

6. The stent of claim 5 wherein the single piece of material comprises a tube.

7. The stent of claim 1 wherein the post members, the interconnecting portions and the leg members are formed from a plurality of pieces and fabricated into a unit.

8. The stent of claim 1 wherein the break-away connection is between the leg members and the interconnecting portions.

9. The stent of claim 8 wherein the break-away connection comprises a score.

10. The stent as defined in claim 1 wherein the post members extend in a first direction.

11. The stent as defined in claim 10 wherein the leg members extend in a second direction, opposite the first direction.

12. A heart valve prosthesis comprising:
    a valve body comprising a flexible material;
    a stent member embedded in the valve body, the stent member comprising a plurality of post members, each post member being connected to an adjacent post member by an interconnecting portion; and
    a plurality of leg members extending from the stent member.

13. The stent as defined in claim 12 wherein the stent includes at least two post members.

14. The stent as defined in claim 13 wherein the stent includes at least two interconnecting portions.

15. The stent as defined in claim 12 wherein the stent includes at least three leg members.

16. The stent as defined in claim 12 wherein the post members, the interconnecting portions and the leg members are formed from a single piece of material.

17. The stent as defined in claim 12 wherein the post members, the interconnecting portions and the leg members are formed from a plurality of pieces and fabricated into a unit.

18. The stent as defined in claim 12 wherein each leg member comprises a break-away connection to the stent member.

19. The stent as defined in claim 12 wherein the post members extend in a first direction.

20. The stent as defined in claim 19 wherein the leg members extend in a second direction, opposite the first direction.

21. A heart valve stent comprising:
    a stent member comprising a plurality of post members, each post member being connected to an adjacent post member by an interconnecting portion; and
    a plurality of leg members extending from the stent member, wherein the post members, the interconnecting portion and the leg members are formed from a plurality of pieces and fabricated into a unit.

* * * * *